(12) United States Patent
Asai et al.

(10) Patent No.: US 11,034,708 B2
(45) Date of Patent: Jun. 15, 2021

(54) LIPID DERIVATIVE FOR NUCLEIC ACID INTRODUCTION

(71) Applicants: NIPPON FINE CHEMICAL CO., LTD., Osaka (JP); SHIZUOKA PREFECTURAL UNIVERSITY CORPORATION, Shizuoka (JP)

(72) Inventors: Tomohiro Asai, Shizuoka (JP); Naoto Oku, Shizuoka (JP); Noriyuki Maeda, Hyogo (JP); Naofumi Fukata, Hyogo (JP); Koji Tomita, Hyogo (JP)

(73) Assignees: NIPPON FINE CHEMICAL CO., LTD., Osaka (JP); SHIZUOKA PREFECTURAL UNIVERSITY CORPORATION, Shizuoka (JP)

( * ) Notice: Subject to any disclaimer, the term of this patent is extended or adjusted under 35 U.S.C. 154(b) by 18 days.

(21) Appl. No.: 16/604,298

(22) PCT Filed: Mar. 1, 2018

(86) PCT No.: PCT/JP2018/007736
§ 371 (c)(1),
(2) Date: Oct. 10, 2019

(87) PCT Pub. No.: WO2018/190017
PCT Pub. Date: Oct. 18, 2018

(65) Prior Publication Data
US 2020/0031853 A1 Jan. 30, 2020

(30) Foreign Application Priority Data

Apr. 11, 2017 (JP) .............................. JP2017-078458

(51) Int. Cl.
*C07F 9/10* (2006.01)
*A61K 47/10* (2017.01)
*A61K 47/24* (2006.01)
*A61K 47/28* (2006.01)
*A61K 45/06* (2006.01)
*A61K 9/16* (2006.01)

(52) U.S. Cl.
CPC ................ *C07F 9/10* (2013.01); *A61K 47/10* (2013.01); *A61K 47/24* (2013.01); *A61K 47/28* (2013.01); *A61K 9/16* (2013.01); *A61K 45/06* (2013.01)

(58) Field of Classification Search
CPC ........ A61K 47/10; A61K 47/24; A61K 47/28; C07F 9/10

USPC ......................................................... 514/75
See application file for complete search history.

(56) References Cited

U.S. PATENT DOCUMENTS

| 3,867,482 A | 2/1975 | Beutel et al. |
| 4,749,805 A | 6/1988 | Eibl |
| 2017/0119887 A1 | 5/2017 | Nishikawa et al. |

FOREIGN PATENT DOCUMENTS

| JP | 48-26936 | 4/1973 |
| JP | 54-84530 | 7/1979 |
| JP | 2005-247750 | 9/2005 |
| JP | 2016-23147 | 2/2016 |

OTHER PUBLICATIONS

International Search Report dated May 29, 2018 in International (PCT) Application No. PCT/JP2018/007736.
Nagata et al., "Fusion of Plant Protoplasts Induced by a Positively Charged Synthetic Phospholipid", Journal of Biosciences, vol. 34C, No. 5-6, 1979, pp. 460-462.
Asai et al., "Dicetyl Phosphate-Tetraethylenepentamine-Based Liposomes for Systemic siRNA Delivery", Bioconjugate Chemistry, 2011, vol. 22, No. 3, pp. 429-435.

*Primary Examiner* — Ana Z Muresan
(74) *Attorney, Agent, or Firm* — Wenderoth, Lind & Ponack, L.L.P.

(57) ABSTRACT

An object is to provide a lipid particle that is not positively charged at a pH of the body fluid (typically in the neutral range), and that enables efficient onset of the effect of a medicinal substance encapsulated in the lipid particle; and to provide a lipid for forming the lipid particle. The object is achieved by the phospholipid represented by formula (1), and a lipid particle containing the phospholipid:

wherein $R^1$ and $R^2$ are identical or different, and represent a chain hydrocarbon group, m represents 1 or 2, n represents 1 or 2, and p represents an integer of 1 to 4.

13 Claims, 13 Drawing Sheets

Fig. 5

| LNP | mix ratio | Size (d.nm) | PDI | ζ-Potential (mV) (in Tris-HCl buffer, pH=7.4) |
|---|---|---|---|---|
| DOP-DD LNP | 1:3 | 174 ± 11 | 0.134 ± 0.10 | -41.1 |
| | 1:5 | 95 ± 5 | 0.207 ± 0.03 | -24.7 |
| DOP-TT LNP | 1:3 | 155 ± 34 | 0.199 ± 0.09 | -14.1 |
| | 1:5 | 102 ± 5 | 0.193 ± 0.01 | -5.99 |

DOP-DD LNP: DOP-DD : DPPC : Chol= 2 : 1 : 2 (molar ratio)
DOP-TT LNP: DOP-TT : DPPC : Chol= 2 : 1 : 2 (molar ratio)

PDI: polydispersity index

LIPID DERIVATIVE FOR NUCLEIC ACID INTRODUCTION

INTRODUCTION

Technical Field

The present invention relates to a lipid derivative for introducing a nucleic acid.

BACKGROUND ART

Recent years have seen enormous promise in RNA interference agents, including small interfering RNA (siRNA), as fascinating pharmaceutical seeds. Although a stream of high-potential seeds have been discovered, an extremely sophisticated delivery system is required for externally administered RNA to exhibit its intrinsic activity in vivo. This is because RNA is readily degraded by nucleases, and poorly penetrates cell membranes. Thus, the commercial viability of RNA interference agents inevitably involves the development of a delivery system.

A known delivery system for medicinal substances, such as RNA, is administration of a medicinal substance encapsulated in a lipid particle. However, administering a negatively charged nucleic acid typically involves the use of a positively charged lipid to cause electrostatic interaction; this raises concerns regarding cytotoxicity (PTL 1).

CITATION LIST

Patent Literature

PTL 1: JP2016-023147A

SUMMARY OF INVENTION

Technical Problem

The present inventors focused on the fact that a lipid particle that is not positively charged at a pH of the body fluid (typically in the neutral range) can reduce cytotoxicity.

An object of the present invention is to provide a lipid particle that is not positively charged at a pH of the body fluid (typically in the neutral range), and that enables efficient onset of the effect of a medicinal substance encapsulated in the lipid particle; and to provide a lipid for forming the lipid particle. Preferably, an object of the present invention is to further provide a lipid particle of a size that can efficiently encapsulate a medicinal substance and/or that is suitable for efficient delivery of a medicinal substance; and to provide a lipid for forming the lipid particle.

Solution to Problem

The present inventors conducted extensive research to achieve the object, and found that a phospholipid represented by formula (1) can form a lipid particle that is not positively charged at a pH of the body fluid (typically in the neutral range), and that enables efficient onset of the effect of a medicinal substance encapsulated in the lipid particle.

Specifically, the present invention includes the following embodiments.

Item 1.

A phospholipid represented by formula (1):

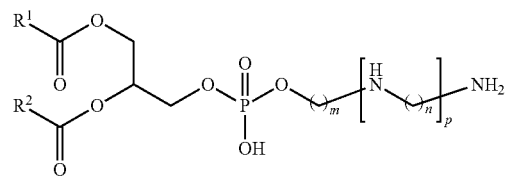

wherein $R^1$ and $R^2$ are identical or different, and represent a chain hydrocarbon group, m represents 1 or 2, n represents 1 or 2, and p represents an integer of 1 to 4.

Item 2.

The phospholipid according to Item 1, wherein the chain hydrocarbon group is an unsaturated chain hydrocarbon group.

Item 3.

The phospholipid according to Item 1 or 2, wherein the chain hydrocarbon group has 12 to 24 carbon atoms.

Item 4.

The phospholipid according to any one of Items 1 to 3, wherein m and n are both 2.

Item 5.

The phospholipid according to any one of Items 1 to 4, wherein p is 1 or 2.

Item 6.

A lipid particle comprising the phospholipid of any one of Items 1 to 5 (phospholipid A).

Item 7.

The lipid particle according to Item 6, in which a medicinal substance is encapsulated.

Item 8.

The lipid particle according to Item 7, wherein the medicinal substance is a polynucleotide.

Item 9.

The lipid particle according to any one of Items 6 to 8, further comprising cholesterol.

Item 10.

The lipid particle according to any one of Items 6 to 9, further comprising a phospholipid having a saturated chain hydrocarbon group (phospholipid B), wherein the phospholipid A has an unsaturated chain hydrocarbon group.

Item 11.

The lipid particle according to Item 10, wherein the phospholipid B is present in an amount of 30 to 70 mol, per 100 mol of the phospholipid A.

Item 12.

A method for producing a lipid particle, the method comprising mixing an alcohol solution containing the phospholipid of any one of Items 1 to 5 with an acid aqueous solution containing a water-soluble medicinal substance.

Item 13.

The method according to Item 12, wherein the water-soluble medicinal substance is a polynucleotide.

Item 14.

The method according to Item 12 or 13, wherein the alcohol solution contains butanol as a solvent.

Item 15.

A medical drug comprising a lipid particle containing the phospholipid of any one of Items 1 to 5, and a medicinal substance.

Advantageous Effects of Invention

The present invention provides a lipid particle that is not positively charged at a pH of the body fluid (typically in the neutral range), and that enables efficient onset of the effect of a medicinal substance encapsulated in the lipid particle; and a lipid for forming the lipid particle. This enables a medicinal substance (e.g., a polynucleotide, such as siRNA) to more efficiently exert its effect, while reducing cytotoxicity.

BRIEF DESCRIPTION OF DRAWINGS

FIG. 5 shows the particle size (Size), particle size distribution (PDI), and zeta potential (ζ-Potential) in the neutral range of lipid particles measured in Example 3.

DESCRIPTION OF EMBODIMENTS

Figure 1:
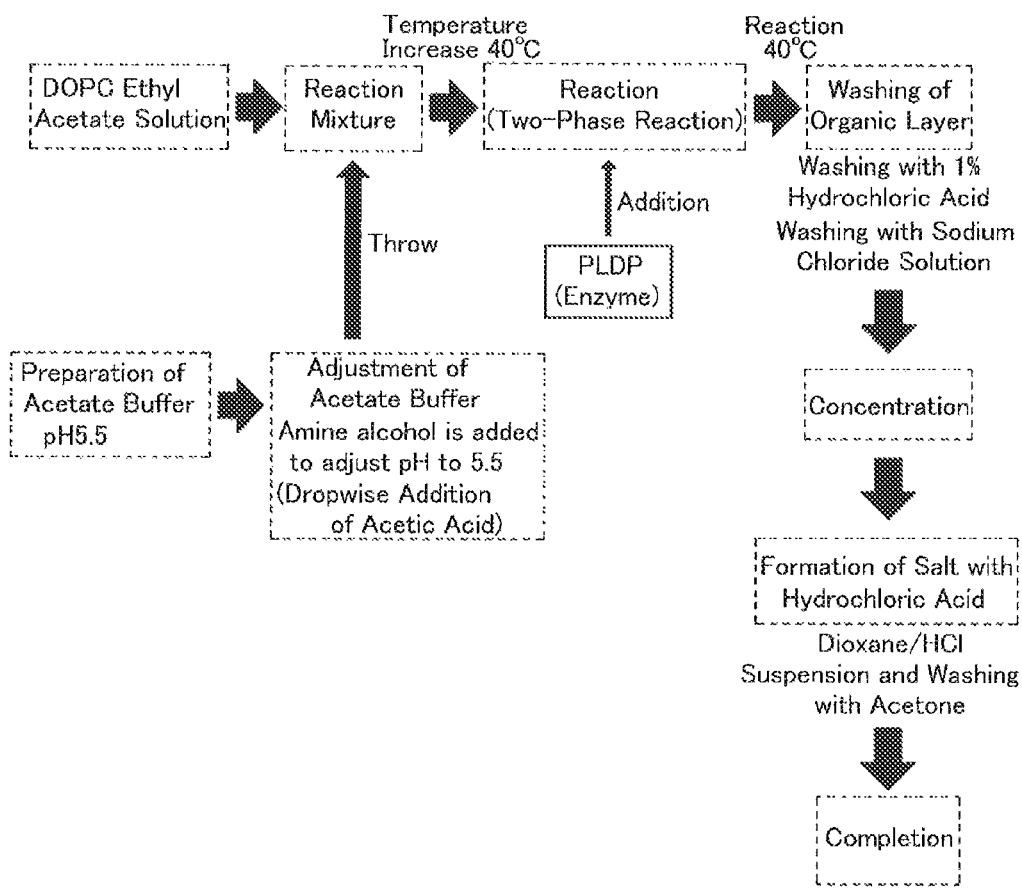
FIG. 1 shows an overview of a synthesis method for DOP-DD (Example 1).

In this specification, the terms "comprise," "contain," and "include" include the concepts of "comprise," "contain," "include" "consist essentially of," and "consist of."

1. Phospholipid

The present invention, according to one embodiment thereof, relates to a phospholipid represented by formula (1):

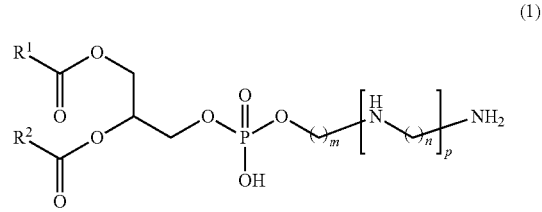

(1)

wherein $R^1$ and $R^2$ are identical or different, and represent a chain hydrocarbon group, m represents 1 or 2, n represents 1 or 2, and p represents an integer of 1 to 4 (which may be referred to as "the phospholipid of the present invention" in this specification). The following describes this phospholipid.

In formula (1), the chain hydrocarbon group represented by $R^1$ and $R^2$ is not particularly limited, as long as the chain hydrocarbon group is a monovalent chain hydrocarbon group; and includes both linear- and branched-chain hydrocarbon groups (preferably linear). The number of carbon atoms of the chain hydrocarbon group is not particularly limited, as long as the chain hydrocarbon group can form a lipid particle; the number of carbon atoms is, for example, 4 to 30, preferably 8 to 26, more preferably 12 to 22, still more preferably 14 to 20, and still yet more preferably 15 to 19. The chain hydrocarbon group includes saturated chain hydrocarbon groups and unsaturated hydrocarbon groups, preferably unsaturated chain hydrocarbon groups, more preferably unsaturated chain hydrocarbon groups having one or more double bonds, and still more preferably unsaturated chain hydrocarbon groups having only one double bond. Examples of the chain hydrocarbon group include butyl, pentyl, hexyl, heptyl, octyl, nonyl, decyl, undecyl, tridecyl, tetradecyl, pentadecyl, 9-pentadecenyl, hexadecyl, heptadecyl, cis-9-heptadecenyl, 11-heptadecenyl, cis,cis-9,12-heptadecadienyl, 9,12,15-heptadecatrienyl, 6,9,12-heptadecanetrienyl, 9,11,13-heptadecanetrienyl, nonadecyl, 8,11-nonadecadienyl, 5,8,11-nonadecatrienyl, 5,8,11,14-nonadecatetraenyl, heneicosyl, tricosyl, cis-15-tricosenyl, pentacosyl, heptacosyl, and nonacosyl.

In formula (1), at least one of $R^1$ and $R^2$ is preferably an unsaturated chain hydrocarbon group, and $R^1$ and $R^2$ are both more preferably an unsaturated chain hydrocarbon group.

In formula (1), m is preferably 2.
In formula (1), n is preferably 2.
In formula (1), m and n are both preferably 2.
In formula (1), p is preferably 1 or 2. From the standpoint of cytotoxicity, p is more preferably 1. From the standpoint of the encapsulation efficiency of a medicinal substance, p is more preferably 2.

The phospholipid of the present invention can be synthesized by various methods. The compound of the present invention can be synthesized, for example, in accordance with or with reference to the following reaction scheme:

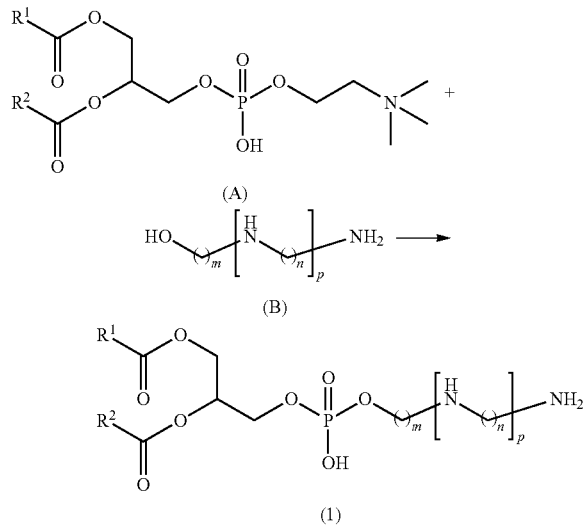

wherein $R^1$, $R^2$, m, n, and p are as defined above.

In this reaction, the compound represented by formula (A) is reacted with the compound represented by formula (B) in the presence of phospholipase D, thereby preparing the compound represented by formula (1).

From the standpoint of yield etc., the amount of the compound represented by formula (B) for use is preferably 2 to 20 mol, and more preferably 5 to 16 mol, per mol of the compound represented by formula (A).

From the standpoint of yield etc., the amount of phospholipase D for use is preferably 100 to 1500 U, and more preferably 400 to 1000 U, per mol of the compound represented by formula (A). One U is defined as an enzyme amount with which 1 micro-mol of a substrate is changed per minute (μmol) under optimum conditions (an acidity at which the chemical reaction proceeds most at a temperature of 30° C.) (1 micro-mol per minute).

This reaction is performed in the presence of a solvent. The solvent is not particularly limited, as long as the solvent can help phospholipase D exert its activity. The solvent preferable for use includes various buffers. A preferable buffer is an acetate buffer. The solvent preferably has a pH of 4 to 7, and more preferably 5 to 6. This reaction system may contain various organic solvents for dissolving the compound represented by formula (A) (e.g., ethyl acetate), in addition to the aqueous solvent.

This reaction is typically performed by mixing a solution of the compound represented by formula (A) in an organic solvent with a solution of the compound represented by formula (B) in an aqueous solvent, and adding phospholipase D to the mixture.

In this reaction, additives, in addition to the components described above, may also be suitably used to the degree that the progress of the reaction is not significantly interfered with.

The reaction temperature is not particularly limited, as long as the temperature allows phospholipase D to exert its activity. The reaction temperature is typically 20 to 50° C., and preferably 35 to 45° C.

The reaction time is not particularly limited, as long as the reaction time allows phospholipase D to exert its activity. The reaction time is typically 8 hours to 150 hours, preferably 24 hours to 100 hours, and more preferably 36 hours to 90 hours.

After completion of the reaction, the solvents are evaporated off; and the product can be isolated and purified by typical techniques, such as chromatography and recrystallization. The structure of the product can be identified, for example, by element analysis, MS (FD-MS) analysis, IR analysis, $^1$H-NMR, or $^{13}$C-NMR.

To improve lipid nanoparticle safety, ionizable lipids have been developed and nanoparticulated. Ionizable lipids are positively charged in the acidic range, and the change in net electrical charge in that case is 0→+1. However, the change in net electrical charge of the phospholipid of the present invention (charge-reversible lipid) can be within the range of −1 to +2; the viewpoint is different. The phospholipid of the present invention is even ionized under neutral conditions, and differs from ionizable lipids in physicochemical properties. Because the lipid of the present invention is able to behave as an amphipathic lipid under neutral conditions, the lipid can offer the prospect of higher stability and higher safety.

The use of the phospholipid of the present invention enables the formation of a lipid particle that is not positively charged at a pH of the body fluid (typically in the neutral range), and that enables efficient onset of the effect of a medicinal substance encapsulated in the lipid particle.

2. Lipid Particle

The present invention, according to one embodiment thereof, relates to a lipid particle (in this specification, "the lipid particle of the present invention") containing the phospholipid of the present invention (in this specification, "phospholipid A"). The following describes this lipid particle.

Figure 9:
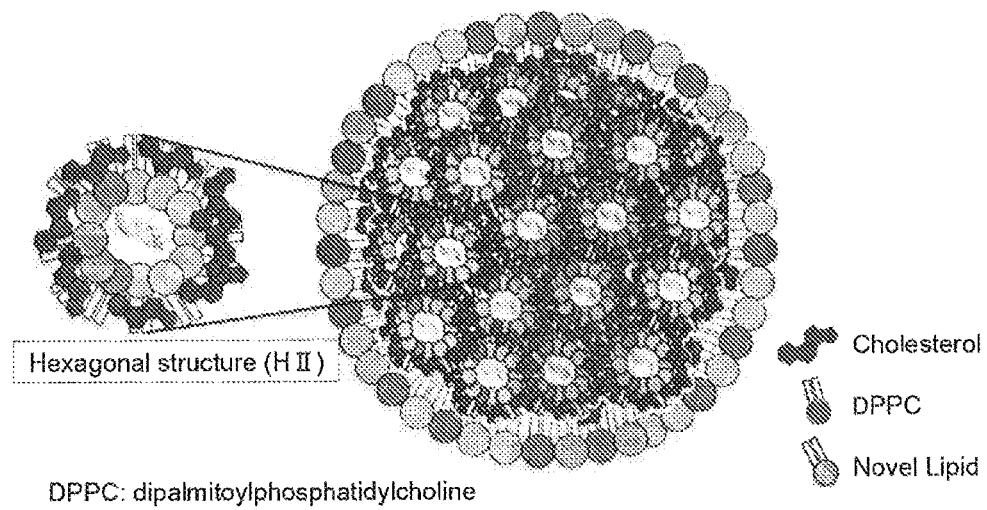
FIG. 9 is a diagram that illustrates a preferable embodiment of the lipid particle of the present invention. Novel Lipid refers to the phospholipid of the present invention. In the graphics of DPPC and Novel Lipid, the circular parts indicate a hydrophilic portion, and the two-stick parts indicate a hydrophobic portion.

The lipid particle of the present invention is not particularly limited, as long as it contains the phospholipid of the present invention as a component lipid of the particle. The phospholipid of the present invention contained in the lipid particle may be one type alone, or a combination of two or more types. The lipid particle of the present invention is, for example, formed such that an amphipathic lipid containing the phospholipid of the present invention forms the outer layer, and the lipid molecules are lined with their hydrophilic portions facing outward. Examples of the lipid particle include particles having the outer layer formed from a lipid monolayer membrane, and particles having the outer layer formed from a lipid bilayer membrane. The lipid particle is preferably a particle having the outer layer formed from a lipid monolayer membrane, and more preferably a particle having the outer layer formed from a lipid monolayer membrane in which amphipathic lipid molecules are lined with their hydrophilic portions facing outward. The inner layer of the particle may be composed of a homogeneous aqueous phase or a homogeneous oil phase, and the inner layer preferably contains one or multiple reverse micelles. FIG. 9 shows a preferable embodiment of the lipid particle of the present invention.

The particle size of the lipid particle of the present invention is not particularly limited. The particle size is preferably nanosize; and is specifically, for example, 10 to 700 nm, preferably 20 to 500 nm, more preferably 40 to 250 nm, still more preferably 60 to 200 nm, still yet more preferably 70 to 150 nm, and particularly preferably 80 to 120 nm.

The lipid particle of the present invention is not positively charged at a pH of the body fluid (typically in the neutral range). More specifically, the lipid particle of the present invention has a zeta potential of −80 to −1 mV, −50 to −1 mV, −40 to −1 mV, −30 to −1 mV, −30 to −10 mV, −30 to −15 mV, or −30 to −20 mV in a Tris-HCl buffer with a pH of 7.4.

The lipid particle of the present invention has a pKa of preferably 6 or more, and less than 7.

The lipid particle of the present invention may contain other lipids as a lipid component of the particle, in addition to the phospholipid of the present invention. Specific examples of such lipids include phospholipids, glycolipids, sterols, and saturated or unsaturated fatty acids.

Specific examples of phospholipids include phosphatidylcholines, such as dilauroylphosphatidylcholine, dimyristoylphosphatidylcholine, dipalmitoylphosphatidylcholine, distearoylphosphatidylcholine, dioleoylphosphatidylcholine, dilinoleoylphosphatidylcholine, myristoylpalmitoylphosphatidylcholine, myristoylstearoylphosphatidylcholine, and palmitoylstearoylphosphatidylcholine; phosphatidylglycerols, such as dilauroylphosphatidylglycerol, dimyristoylphosphatidylglycerol, dipalmitoylphosphatidylglycerol, distearoylphosphatidylglycerol, dioleoylphosphatidylglycerol, dilinoleoylphosphatidylglycerol, myristoylpalmitoylphosphatidylglycerol, myristoylstearoylphosphatidylglycerol, and palmitoylstearoylphosphatidylglycerol; phosphatidylethanolamines, such as dilauroylphosphatidylethanolamine, dimyristoylphosphatidylethanolamine, dipalmitoylphosphatidylethanolamine, distearoylphosphatidylethanolamine, dioleoylphosphatidylethanolamine, dilinoleoylphosphatidylethanolamine, myristoylpalmitoylphosphatidylethanolamine, myristoylstearoylphosphatidylethanolamine, and palmitoylstearoylphosphatidylethanolamine; phosphatidylserine; phosphatidic acid; phosphatidylinositol; sphingomyelin; cardiolipin; egg yolk lecithin; soybean lecithin; and hydrogenated products thereof. These phospholipids may be those modified with a water-soluble polymer, such as PEG.

Specific examples of glycolipids include glyceroglycolipids, such as diglycosyl diglyceride, digalactosyl diglyceride, galactosyl diglyceride, and glycosyl diglyceride; glycosphingolipids, such as galactosyl cerebroside, and ganglioside; and stearyl glucoside, and esterified stearyl glycoside.

Specific examples of sterols include cholesterol, cholesteryl hemisuccinate, lanosterol, dihydrolanosterol, desmosterol, dihydrocholesterol, phytosterol, phytosterol, stigmasterol, timosterol, ergosterol, sitosterol, campesterol, and brassicasterol. The lipid particle preferably contains a sterol as a lipid component of the liposome membrane, particularly because of its action to stabilize the liposome membrane, and to adjust the fluidity of the liposome membrane.

Specific examples of saturated or unsaturated fatty acids include saturated or unsaturated fatty acids having 10 to 22 carbon atoms, such as decanoic acid, myristic acid, palmitic acid, stearic acid, arachidonic acid, oleic acid, and docosanoic acid.

These lipids may be used singly, or in a combination of two or more.

The lipid particle of the present invention preferably contains a phospholipid other than the phospholipid of the present invention (in this specification, "phospholipid B"), and a sterol. When the phospholipid of the present invention has an unsaturated chain hydrocarbon group, phospholipid B preferably has a saturated chain hydrocarbon group. Phospholipid B is preferably phosphatidylcholine, and particularly preferably dipalmitoyl phosphatidylcholine. The sterol is preferably cholesterol.

When the lipid particle of the present invention contains phospholipid B, the phospholipid B is present in an amount of, for example, 15 to 100 mol, preferably 30 to 70 mol, more preferably 40 to 60 mol, and still more preferably 45 to 55 mol, per 100 mol of the phospholipid of the present invention. Alternatively, the phospholipid B is present in an amount of, for example, 5 to 70 mol, preferably 10 to 40 mol, more preferably 15 to 30 mol, and still more preferably 17 to 27 mol, per 100 mol of the phospholipid of the present invention.

When the lipid particle of the present invention contains a sterol, the sterol is present in an amount of, for example, 30 to 200 mol, preferably 60 to 140 mol, more preferably 80 to 120 mol, still more preferably 90 to 110 mol, and still yet more preferably 95 to 105 mol, per 100 mol of the phospholipid of the present invention.

When the lipid particle of the present invention contains phospholipid B and a sterol, phospholipid B is present in an amount of, for example, 15 to 100 mol, preferably 30 to 70 mol, more preferably 40 to 60 mol, and still more preferably 45 to 55 mol, per 100 mol of the sterol. Alternatively, phospholipid B is present in an amount of, for example, 5 to 70 mol, preferably 10 to 40 mol, more preferably 15 to 30 mol, and still more preferably 17 to 27 mol, per 100 mol of the phospholipid of the present invention.

The phospholipid of the present invention and optionally added other lipids (in a preferable embodiment, phospholipid B and a sterol) are present in a total amount of, for example, 50 mol % or more, preferably 70 mol % or more, more preferably 90 mol % or more, still more preferably 95 mol % or more, and still yet more preferably 99 mol % or more, per 100 mol % of the lipid component of the lipid particle of the present invention.

In the lipid particle of the present invention, part of the phospholipid is preferably modified with a water-soluble polymer, such as PEG. A phospholipid modified with PEG is present in an amount of, for example, 1 to 50 mol %, preferably 2 to 30 mol %, more preferably 3 to 20 mol %, and still more preferably 4 to 15 mol %, per 100 mol % of the lipid component of the lipid particle of the present invention.

In the lipid particle of the present invention, a medicinal substance is preferably encapsulated. The medicinal substance is not particularly limited, and examples include polynucleotides, peptides, proteins, carbohydrates, and low-molecular compounds. The medicinal substance is preferably negatively charged, and preferably water-soluble. Such a medicinal substance suitably usable is a polynucleotide. The target disease of the medicinal substance is not particularly limited, and examples include cancer (in particular, solid cancer).

The polynucleotide is not particularly limited, as long as the polynucleotide can function as a medicinal substance. Examples include siRNA, miRNA, antisense nucleic acids, expression vectors therefor, expression vectors for proteins, nucleic acids for genome editing (e.g., guide RNAs, Cas protein expression vectors, and TALEN expression vectors), and nucleic acid vaccines.

The polynucleotide may have a known chemical modification as described below. To prevent degradation by hydrolases such as nucleases, the phosphoric residue (phosphate) of each nucleotide may be replaced with a chemically modified phosphoric residue, such as phosphorothioate (PS), methylphosphonate, or phosphorodithionate. The hydroxyl group at position 2 of the sugar (ribose) of each ribonucleotide may be replaced with —OR (R represents, for example, $CH_3$ (2'-O-Me), $CH_2CH_2OCH_3$ (2'-O-MOE), $CH_2CH_2NHC(NH)NH_2$, $CH_2CONHCH_3$, or $CH_2CH_2CN$). Additionally, the base moiety (pyrimidine, purine) may be chemically modified; for example, introduction of a methyl group or a cationic functional group into position 5 of the pyrimidine base, or replacement of the carbonyl group at position 2 into thiocarbonyl. The phosphoric moiety or hydroxyl moiety may also be modified with, for example, a biotin, an amino group, a lower alkyl amine group, or an acetyl group. However, chemical modification is not limited thereto. Additionally, BNA (LNA), for example, whose sugar moiety conformation is immobilized in N form by bridging the 2'oxygen and 4'carbon in the sugar moiety of the nucleotide, can also be preferably used.

The medicinal substance is preferably contained in the inner layer of the lipid particle of the present invention. When the medicinal substance is a polynucleotide, the medicinal substance is preferably contained within a reverse micelle in the inner layer.

The molar ratio of the lipid component of the lipid particle of the present invention to the medicinal substance (the lipid component of the lipid particle of the present invention/the medicinal substance, mol/mol) is, for example, 500 or more, preferably 1000 or more, more preferably 1500 or more, still more preferably 1900 or more, still yet more preferably 2500 or more, and particularly preferably 3200 or more, when, for example, the medicinal substance is a polynucleotide, such as siRNA. The upper limit of the molar ratio is not particularly limited; and is, for example 10000, 7000, or 5000.

The lipid particle of the present invention may contain other components in addition to the components described above. Examples of other components include membrane stabilizers, charged substances, antioxidants, membrane proteins, polyethylene glycol (PEG), antibodies, peptides, and sugar chains.

An antioxidant can be added to prevent oxidation of the membrane, and is optionally used as a component of a membrane. Examples of antioxidants used as a component of a membrane include butylated hydroxytoluene, propyl gallate, tocopherol, tocopheryl acetate, mixed tocopherol concentrate, vitamin E, ascorbic acid, L-ascorbyl stearate, ascorbyl palmitate, sodium hydrogen sulfite, sodium sulfite, sodium edetate, erythorbic acid, and citric acid.

A membrane protein can be added to add functions to a membrane, or to stabilize the structure of a membrane; and is optionally used as a component of a membrane. Examples of membrane proteins include peripheral membrane proteins, integral membrane proteins, albumin, and recombinant albumins.

The other components are present in an amount of, for example, 10% or less, preferably 5% or less, more preferably 2% or less, and still more preferably 1% or less, based on 100 mass % of the lipid particle of the present invention.

The lipid particle of the present invention can be produced in accordance with or with reference to a known production method for a lipid particle. The lipid particle of the present invention can be produced preferably by a method including the step of mixing an alcohol solution containing the phospholipid of the present invention with an acid aqueous solution containing a water-soluble medicinal substance (step 1).

The alcohol as a solvent of the alcohol solution is not particularly limited, as long as the alcohol can dissolve the phospholipid. From the standpoint of solubility, the alcohol is preferably butanol, and more preferably t-butanol.

The acid aqueous solution typically contains an acid in addition to a water-soluble medicinal substance and water, which is a solvent. Examples of the acid include organic acids and inorganic acids, with organic acids being preferable. Examples of organic acids include maleic acid, formic acid, acetic acid, propionic acid, folic acid, isobutyric acid, valeric acid, isovaleric acid, pyruvic acid, oxalic acid, malonic acid, succinic acid, glutaric acid, ketoglutaric acid, adipic acid, lactic acid, tartaric acid, fumaric acid, oxaloacetic acid, malic acid, isocitric acid, citric acid, benzoic acid, phthalic acid, isophthalic acid, terephthalic acid, hemimellitic acid, trimellitic acid, trimesic acid, mellophanic acid, prehnitic acid, pyromellitic acid, mellitic acid, methanesulfonic acid, benzenesulfonic acid, p-toluenesulfonic acid, camphorsulfonic acid, p-toluenesulfinic acid, and benzenesulfinic acid; with citric acid being preferable. Examples of inorganic acids include hydrochloric acid, sulfuric acid, nitric acid, carbonic acid, boric acid, boronic acid, hydrofluoric acid, hypochlorous acid, chlorous acid, chloric acid, perchloric acid, hypobromous acid, bromous acid, bromic acid, perbromic acid, hypoiodous acid, iodous acid, iodic acid, periodic acid, phosphorus acid, phosphoric acid, polyphosphoric acid, chromic acid, permanganic acid, and Amberlyst. The acids may used singly, or in a combination of two or more.

The acid aqueous solution preferably has a pH of 3 to 5.

The mixture ratio of the acid aqueous solution to the alcohol solution (the acid aqueous solution/the alcohol solution, v/v) is, for example, 1.5 to 10, preferably 2 to 8, more preferably 3 to 7, still more preferably 4 to 6, and still yet more preferably 4.5 to 5.5.

Mixing is not particularly limited, as long as the mixing mode allows the phospholipid of the present invention to be mixed with the medicinal substance. Typically, the acid aqueous solution and the alcohol solution are intensely stirred, for example, with a vortex mixer. Although the mixing time period varies depending on the mixing mode, the mixing time period is, for example, 10 seconds to 2 minutes, and preferably 15 seconds to 1 minute.

Step 1 is typically performed with heating. The temperature in step 1 is, for example, 30° C. to 50° C., and preferably 35° C. to 45° C.

After step 1, the obtained mixture is preferably allowed to stand.

The time period during which the mixture is allowed to stand is, for example, 30 seconds to 5 minutes, and preferably 1 minute to 3 minutes.

The temperature at which the mixture is allowed to stand is, for example, 30° C. to 50° C., and preferably 35° C. to 45° C.

Step 1 can also be performed using a reaction system with a microchannel. In this case, the conditions for step 1 can be suitably adjusted according to the reaction system.

3. Application of Lipid Particle

The present invention, according to one embodiment thereof, relates to a medical drug containing the lipid particle of the present invention in which a medicinal substance is encapsulated (in this specification, "the medical drug of the present invention"). The lipid particle of the present invention in which a medicinal substance is encapsulated is also usable as a reagent.

The lipid particle of the present invention enables a medicinal substance (e.g., a polynucleotide, such as siRNA) to exert its effect more efficiently, while reducing cytotoxicity. Thus, the lipid particle of the present invention can suitably be used as a carrier for a medicinal substance.

The content of the active ingredient (i.e., a medicinal substance) in the medical drug of the present invention can be suitably determined, taking into consideration, for example, the type of target disease, target therapeutic effect, administration method, treatment period, patient's age, and patient's body weight. For example, the content of the active ingredient in the medical drug of the present invention may be about 0.0001 parts by weight to 100 parts by weight, based on the entire medical drug of the present invention taken as 100 parts by weight.

The mode of administration of the medical drug of the present invention is not particularly limited, as long as a desired effect is brought about. The medical drug can be administered to mammals including humans through an administration route of either peroral administration or parenteral administration (e.g., intravenous injection, intramuscular injection, subcutaneous administration, rectal administration, transdermal administration, and local administration). The mode of administration is preferably parenteral administration, and more preferably intravenous injection. The dosage forms for peroral administration and parenteral administration and the production methods therefor are well known to those skilled in the art. Such dosage forms can be produced by mixing an active ingredient with a pharmaceutically acceptable carrier and other components, in accordance with a standard method.

The dosage form for parenteral administration includes injectable preparations (e.g., drip injectable drugs, intravenous injectable drugs, intramuscularly injectable drugs, subcutaneously injectable drugs, and intradermally injectable drugs), drugs for external use (e.g., ointments, cataplasms, and lotions), suppository inhalants, eye drops, ophthalmic ointments, nasal drops, ear drops, and liposome drugs. For example, an injectable preparation can be prepared by dissolving the lipid particle of the present invention in injectable distilled water; and a solubilizing agent, a buffer, a pH adjuster, a tonicity agent, a soothing agent, a preservative, a stabilizer etc., can be optionally added thereto. The medical drug may be a freeze-dried formulation that is prepared into a drug when needed.

The medical drug of the present invention may further contain other medicinal agents effective in the treatment or prevention of diseases. The medical drug of the present invention may also optionally contain components, such as antiseptic drugs, antiphlogistics, cell activators, vitamins, and amino acids.

For the carrier for use in preparing the medical drug of the present invention, those typically used in this technical field, such as excipients, binders, disintegrants, lubricants, colorants, and flavoring agents, can be used; and stabilizers, emulsifiers, absorption promoters, surfactants, pH adjusters, antiseptics, antioxidants, fillers, moisturizers, surface activators, dispersants, buffers, preservatives, solubilizing agents, soothing agents, and the like can also optionally be used.

The dosage of the medical drug of the present invention can be determined by a practical physician, taking into consideration various factors, such as the administration route; type of disease; degree of symptoms; patient's age, gender, and body weight; severity of disease; pharmacological findings such as pharmacokinetics and toxicological characteristics; whether a drug delivery system is used; and whether the medical drug is administered as part of a combination with other medicinal substances. The dosage of the medical drug of the present invention may be, for example, about 1 μg/kg (body weight) to 10 g/kg (body weight) per day. The dose schedule of the medical drug of the present invention can also be determined while taking into consideration the same factors as those for the dosage. For example, the medical drug of the present invention can be administered in the dosage per day described above once daily to once per month.

EXAMPLES

The following describes the present invention in detail with reference to Examples. However, the present invention is not limited to these Examples.

Example 1-1: Synthesis 1 of
Dioleoylphosphate-Diethylenediamine Conjugate
(DOP-DD or DOP-DEDA)

DOP-DEDA was synthesized in accordance with the following scheme. FIG. 1 shows an overview of the synthesis method.

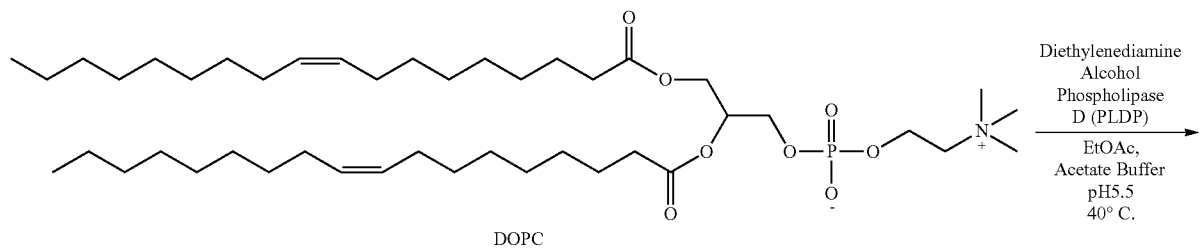

DOPC

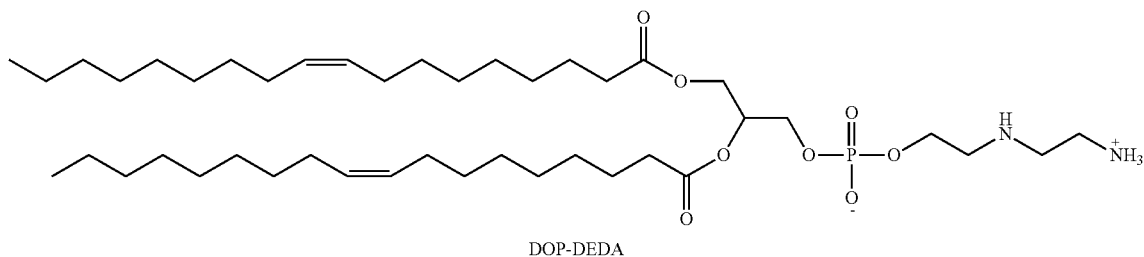

DOP-DEDA

A 0.5M acetate buffer with a pH of 5.5 in which 1.84 g of 2-(2-aminoethylamino)ethanol (17.8 mmol) was dissolved was added to a mixture prepared by dissolving 1.0 g (1.3 mol) of DOPC in ethyl acetate, and this mixture was heated to 40° C. After heating, PLDP (Asahi Kasei Pharma Corporation, phospholipase D) (600 U) was added thereto, followed by stirring for 48 hours. The mixture was stirred until consumption of DOPC was confirmed by TLC analysis. One unit is defined as an enzyme amount with which 1 micro-mol of a substrate is changed per minute (µmol) under optimum conditions (an acidity at which the chemical reaction proceeds most at a temperature of 30° C.) (1 micro-mol per minute).

Figure 2:
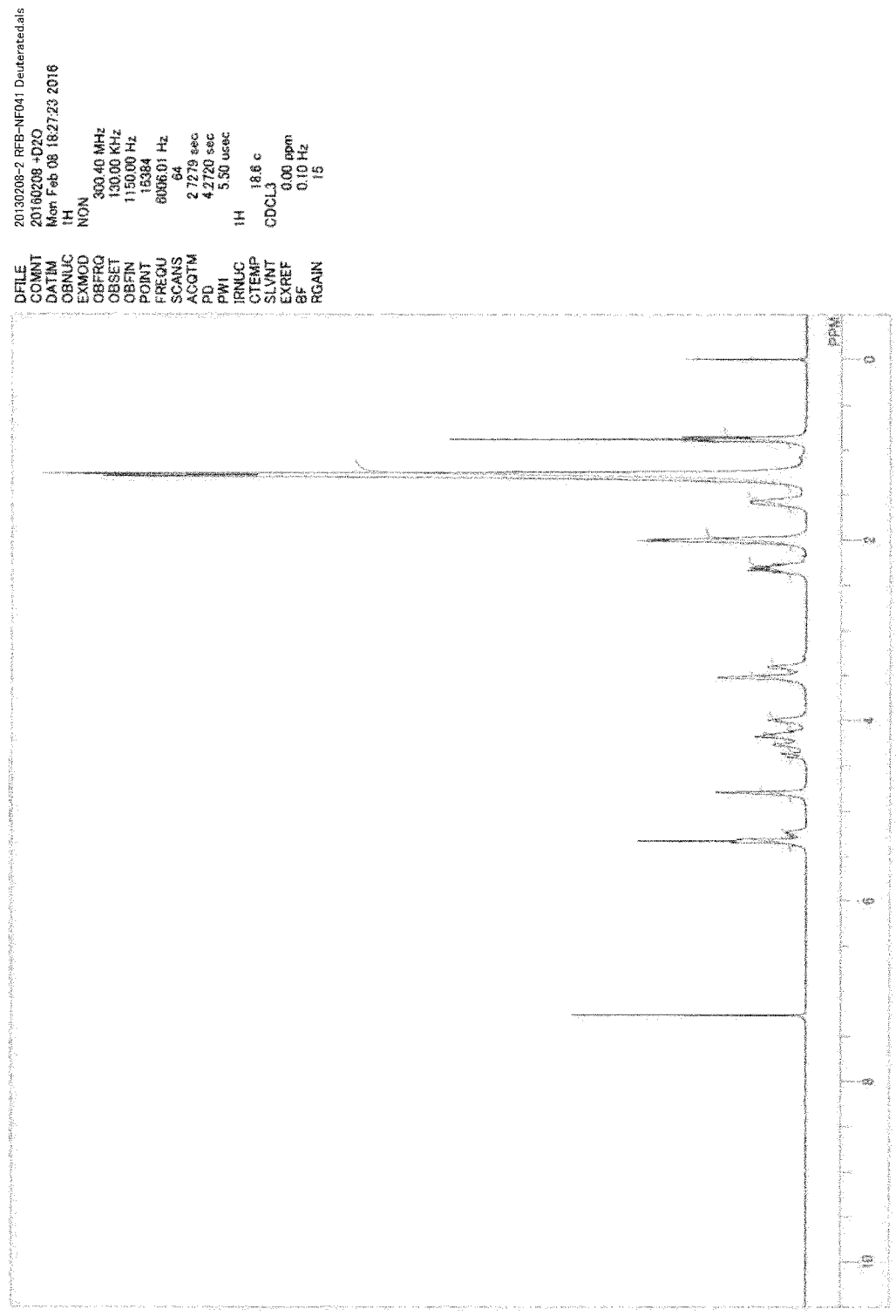
FIG. 2 shows an NMR chart of the DOP-DD synthesized in Example 1.

The reaction mixture was diluted with chloroform and methanol (chloroform:methanol=6:1), and washed with 1% hydrochloric acid and a 20% sodium chloride solution. The reaction mixture was concentrated under reduced pressure; and concentrated to dryness, thereby obtaining 0.72 g of a concentrate. 0.36 g of the obtained crude reaction product was dissolved in 4 ml of dioxane; and 2 ml of dioxane/4M HCl was added dropwise thereto, followed by stirring at room temperature. After ice-cooling, acetone was added, and the mixture was stirred for 1 hour. The precipitated white crystal was suspended and washed with acetone three times. The obtained crystal was vacuum-dried overnight, thereby obtaining 0.20 g of a white crystal (yield: 40%). FIG. 2 shows an NMR chart.

Example 1-2: Synthesis 2 of Dioleoylphosphate-Diethylenediamine Conjugate (DOP-DD or DOP-DEDA)

DOP-DEDA was synthesized in accordance with the scheme of Example 1-2.

A 0.5M acetate buffer with a pH of 5.5 in which 55.21 g of 2-(2-aminoethylamino)ethanol (904 mmol) was dissolved was added to a mixture prepared by dissolving 30.06 g (38.2 mmol) of DOPC in ethyl acetate, and this mixture was heated to 40° C. After heating, PLDP (Asahi Kasei Pharma Corporation, phospholipase D) (14400 U) was added thereto, followed by stirring for 21 hours. The mixture was stirred until consumption of DOPC was confirmed by TLC analysis.

The reaction mixture was diluted with chloroform and methanol (chloroform:methanol=6:1), and washed with 1% hydrochloric acid and a 20% sodium chloride solution. The reaction mixture was concentrated under reduced pressure; and concentrated to dryness, thereby obtaining 28.83 g of a concentrate. 5.00 g of the obtained crude reaction product was dissolved in 55 ml of dioxane, and cooled with ice. 27.5 ml of dioxane/4M HCl was added dropwise thereto, followed by stirring for 30 minutes. After stirring, the precipitated pale-yellow crystal was filtered off; and the crystal was suspended and washed with acetone three times. The obtained crystal was vacuum-dried overnight, thereby obtaining 3.10 g of a pale-yellow crystal. 2.80 g of the obtained pale-yellow crystal was dissolved in 55 mL of THF. After ice-cooling, 140 ml of acetone was added dropwise, followed by stirring in an ice bath for 30 minutes. After stirring, the precipitated pale-yellow crystal was filtered off, and the crystal was suspended and washed with acetone five times. The obtained crystal was vacuum-dried overnight, thereby obtaining 2.61 g of a pale-yellow crystal (yield 56%).

Example 2: Synthesis of Dioleoylphosphate-Triethylenetriamine Conjugate (DOP-TT or DOP-TETA)

Figure 3:
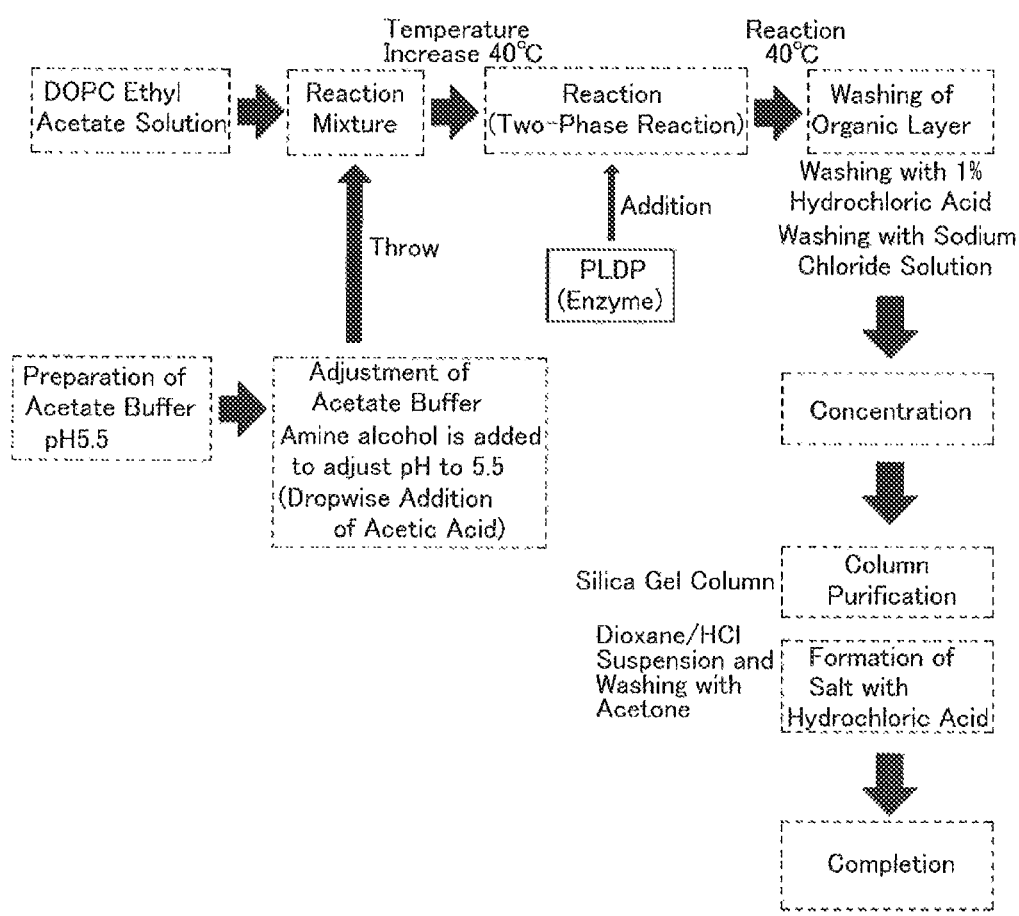
FIG. 3 shows an overview of a synthesis method for DOP-TT (Example 2).

DOP-TETA was synthesized in accordance with the following scheme. FIG. 3 shows an overview of the synthesis method.

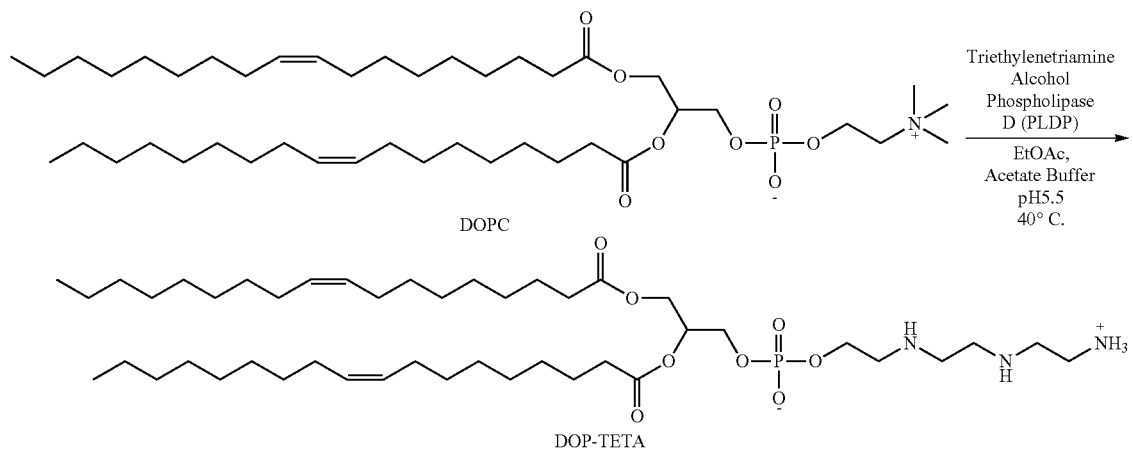

A 0.1M acetate buffer with a pH of 5.5 in which 1.53 g (10.4 mmol) of hydroxyethyl diethylenetriamine was dissolved was added to a mixture prepared by dissolving 1.0 g (1.3 mmol) of DOPC in ethyl acetate, and this mixture was heated to 40° C. After heating, PLDP (810 U) was added thereto, followed by stirring for 72 hours. The mixture was stirred until consumption of DOPC was confirmed by TLC analysis.

Figure 4:
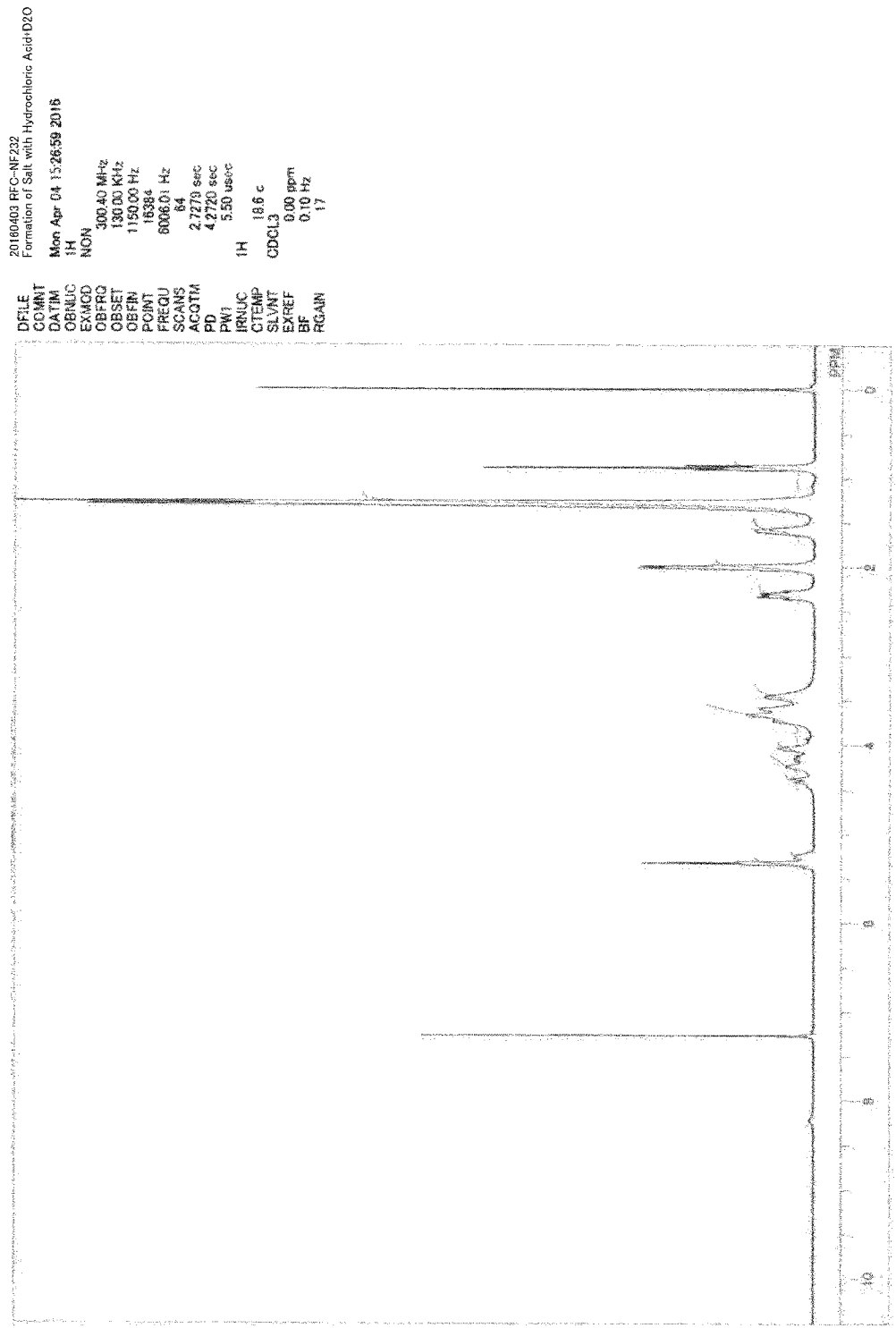
FIG. 4 shows an NMR chart of the DOP-TT synthesized in Example 2.

The reaction mixture was diluted with ethyl acetate, and washed with 1% hydrochloric acid and a 20% sodium chloride solution. The reaction mixture was concentrated under reduced pressure; and concentrated to dryness, thereby obtaining 0.80 g of a concentrate. The concentrate was purified by silica gel column chromatography (chloroform/methanol/water=60/30/5); and the corresponding concentrate was concentrated, followed by dissolving the fraction in 3 ml of dioxane. Subsequently, 5 ml of dioxane/4M HCl was added to the solution of the concentrate in dioxane with ice-cooling, and 13 ml of acetone was added. The precipitated white wax-like substance was subjected to suction filtration; and dried under reduced pressure, thereby obtaining 33 mg of a corresponding white wax-like substance (yield 3%). FIG. 4 shows an NMR chart.

Example 3: Production of Lipid Particles and Measurement of Various Physical Properties

Example 3-1: Production of Lipid Particles siRNA was added to 1 mM citric acid buffer (pH 4.0), thereby preparing an acidic aqueous solution of siRNA (40° C., siRNA concentration: 571 nM). Separately, lipids (DOP-DD or DOP-TT, dipalmitoyl phosphatidylcholine (DPPC), and cholesterol (Chol)) were added to t-butanol in a molar ratio of 2:1:2 (DOP-DD or DOP-TT:DPPC:Chol), thereby preparing a phospholipid alcohol solution (40° C., lipid concentration: 10 mM). A 3- or 5-fold volume of the acidic aqueous solution of siRNA was added to the phospholipid alcohol solution, immediately followed by vortex for 30 seconds. The obtained mixture was incubated at 40° C. for 2 minutes, thereby obtaining lipid particles. Finally, t-butanol was removed by dialysis.

Example 3-2: Measurement of Various Physical Properties

The lipid particles were diluted 20-fold with RNase free water, and then the particle size and polydispersity index (PDI) were measured with a Zetasizer Nano ZS (Malvern). The lipid nanoparticles were also diluted 20-fold with a 10 mM Tris-HCl buffer (pH=7.4), and the $\zeta$-Potential was measured.

FIG. 5 shows the results. As indicated in FIG. 5, the phospholipid particles prepared using DOP-DD or DOP-TT were excellent in particle size and particle size distribution. Although a positive zeta potential under physiological conditions (in the neutral range) leads to concerns regarding cytotoxicity, the obtained phospholipid particles had a negative zeta potential in the neutral range; thus, the phospholipid particles were also excellent in this point.

Example 4: Production of Lipid Particles and Measurement of Encapsulation Efficiency

Example 4-1: Production of Lipid Particles

The procedure of Example 3-1 was repeated, except that a 5-fold volume of an acidic aqueous solution of siRNA was added to a phospholipid alcohol solution; and the molar ratio of siRNA to the lipids (siRNA:lipid) was 1:700, thereby producing lipid particles.

Example 4-2: Measurement of Encapsulation Efficiency

The measurement was performed using an RNA assay reagent (RiboGreen reagent, Thezmo Fisher Scientific), specifically as described below. A 2% Triton-X 100 or RNase free water was added to a lipid particle solution. The obtained solution, RNase free water, and a RiboGreen reagent were mixed in the wells of a 96-well black plate. The plate was shaken for 5 minutes, and the fluorescence intensity in each well was measured. The encapsulation efficiency of siRNA in the lipid particles was calculated using the following equation with the measured fluorescence intensity.

The encapsulation efficiency (%)=(the fluorescence intensity of total siRNA−the fluorescence intensity of free siRNA)/(the fluorescence intensity of total siRNA)

As a result, the encapsulation efficiency of the case in which DOP-DD was used as a phospholipid was 96.4%, and the encapsulation efficiency in which DOP-TT was used as a phospholipid was 99.4%.

Example 5: Production of Lipid Particles and Measurement of pKa

Example 5-1: Production of Lipid Particles

Lipid particles were produced using DOP-DD, DPPC, and Chol as lipids in the same manner as in Example 3-1.

Example 5-2: Measurement of pKa

An assay buffer (composition: 20 mM sodium phosphate, 25 mM citric acid, 20 mM ammnonium acetate, and 150 mM sodium chloride) was prepared. The pH of the assay buffer was adjusted to 4.5, 5.0, 6.0, 6.5, 7.0, 7.4, 8.0, 8.5, 9.0, or 9.5. The lipid particles were added to the assay buffer to give a concentration of 20 μM; and TNS (2-(p-toluidinyl)naphthalene-6-sulphonic acid) was further added thereto to give a concentration of 6 μM, followed by measuring the fluorescence intensity ($\lambda_{ex}$=321 nm, $\lambda_{em}$=431 nm).

Figure 6:
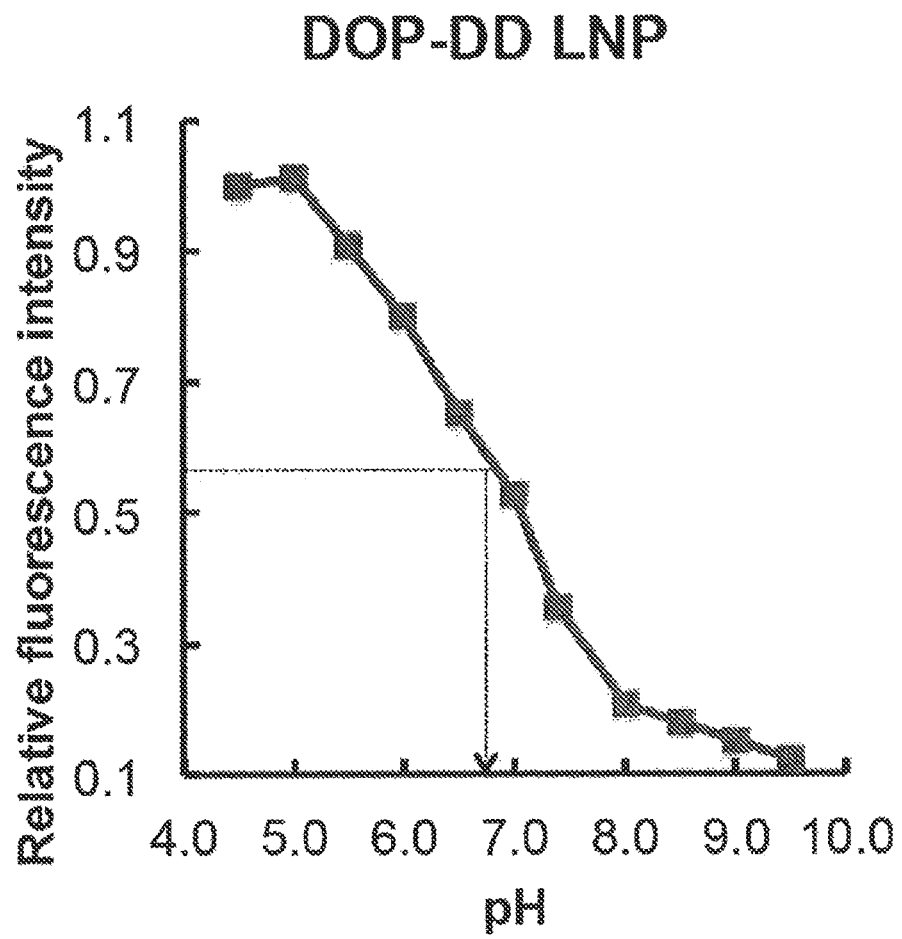
FIG. 6 shows the measurement results of pKa of the lipid particles measured in Example 5. The vertical axis indicates a relative value of the TNS-derived fluorescence intensity, and a pH of the assay buffer is indicated.

FIG. 6 shows the results. FIG. 6 indicates 6.0<pKa<7.0. This reveals that phospholipid particles obtained using DOP-DD are not positively charged ("positively charged" raises concerns regarding cytotoxicity) under physiological conditions (in the neutral range).

Example 6: Production of Lipid Particles and Gene Silencing Test 1

Example 6-1: Production of Lipid Particles

The procedure of Example 3-1 was repeated, except that DOP-DD, dioleoylphosphatidylethanolamine (PD-13) having a cell-membrane-permeable peptide (protamine-13: RRRRRRGGRRRRG) linked thereto, DPPC, and Chol were used as lipids (molar ratio: 37.7:5.7:18.9:37.7 (DOP-DD:PD-13:DPPC:Chol)); siRNA for Lamin A/C was used for the siRNA; and the molar ratio of siRNA to the lipids (siRNA:lipids) was 1:2100 or 1:3500, thereby producing lipid particles.

Example 6-2: Gene Silencing Test

Hela cells were seeded into a 6-well plate (1.5×10$^5$ cells/well), and cultured at 37° C. for 24 hours. A lipid particle solution (containing 60 pmol of siRNA) and a composite solution of siRNA (containing 80 pmol of siRNA) were each added dropwise to the wells, and cultured at 37° C. for 24 hours. The total RNA was extracted from the cells using a TRIzol reagent (Thermo Fisher Scientific), and cDNA was synthesized from the total RNA. The mRNA level of Lamin A/C was quantified by real-time PCR with cDNA as a template.

Figure 7:
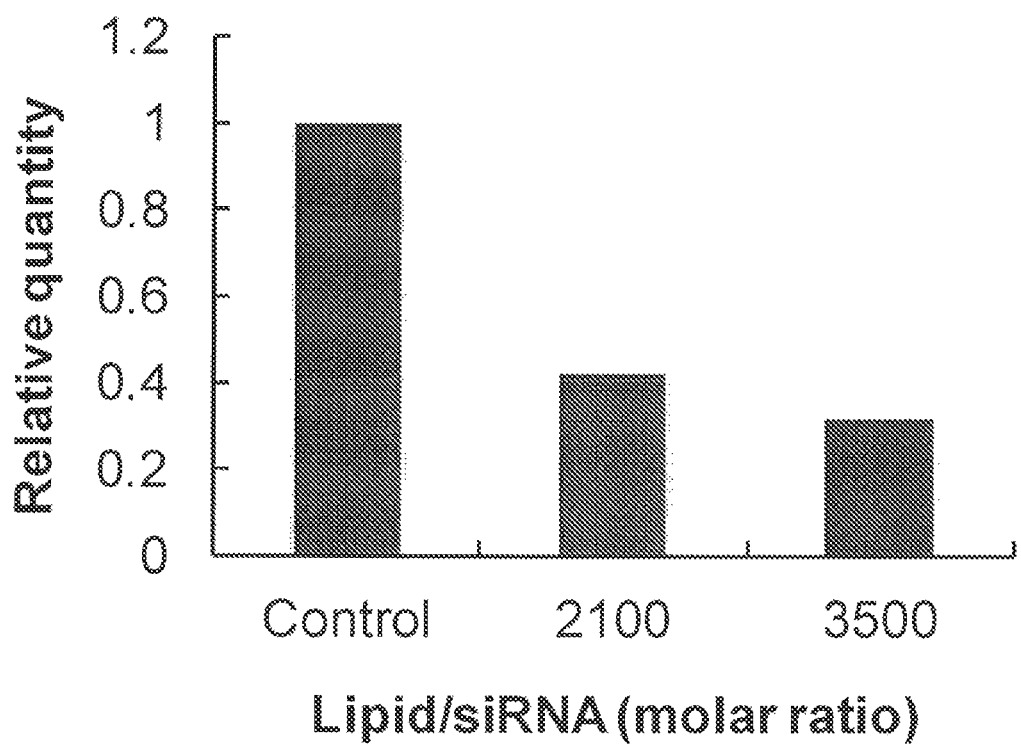
FIG. 7 shows the results of quantified mRNA level of Lamin A/C measured in Example 6. The vertical axis indicates a relative value of the mRNA level of Lamin A/C. The horizontal axis indicates the type of the samples. Control is a negative control, and 2100 and 3500 each indicate a lipid particle solution (the numbers indicate the lipid/siRNA molar ratio).

FIG. 7 shows the results. The phospholipid particles prepared using DOP-DD were confirmed to be able to efficiently knock down a gene.

Example 7: Production of Lipid Particles and Gene Silencing Test 2

The procedure of Example 6 was repeated, except that siRNA-introduced cells were dissolved in 0.1% SDS to extract the protein, and the level of Lamin A/C protein was quantified by western blotting.

Figure 8:
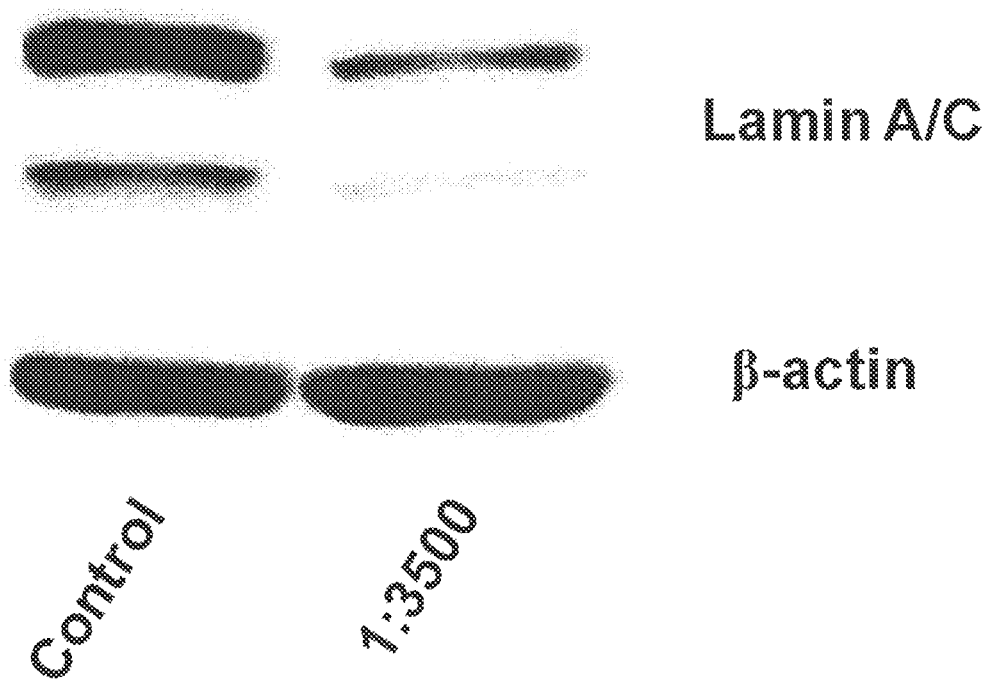
FIG. 8 shows the results of the quantified Lamin A/C protein level measured in Example 7. The upper part illustrates the band of Lamin A/C protein; and the lower part illustrates the band of β-actin protein, which is a control. The bottom of the photograph indicates the type of the samples. Control is a negative control, and 3500 indicates a lipid particle solution (the number indicates the lipid/siRNA molar ratio).

FIG. 8 shows the results. The phospholipid particles prepared using DOP-DD were confirmed to be able to efficiently knock down a gene.

Example 8: Production of Lipid Particles and Hemolysis Test with pH Variations

Example 8-1: Production of Lipid Particles siRNA was added to 1 mM citric acid buffer (pH 4.0), thereby preparing an acidic aqueous solution of siRNA (40° C., siRNA concentration: 571 nM). Separately, lipids (DOP-DD, dipalmitoyl phosphatidylcholine (DPPC), and cholesterol (Chol)) were added to t-butanol in a molar ratio (DOP-DD:DPPC:Chol) of 45:10:45, thereby preparing a lipid alcohol solution (40° C., lipid concentration: 10 mM). A 5-fold volume of an acidic aqueous solution of siRNA was added to the phospholipid alcohol solution, immediately followed by vortex for 30 seconds. Thereafter, dialysis was performed with ultrapure water to remove t-butanol, thereby obtaining lipid particles.

Example 8-2: Production of Control Lipid Particles

Lipids (dioleoyl phosphatidyl diethylenetriamine (DOP-DETA), DPPC, and Chol) were added to t-butanol in a molar ratio of 2:1:2, thereby preparing a lipid alcohol solution. Other operations were performed in the same manner as in Example 8-1, thereby producing lipid particles.

Example 8-3: Hemolysis Test with pH Variations

500 μL of preserved bovine blood (Nippon Bio-Test Laboratories Inc.) and 1 mL of 1×PBS were stirred and centrifuged (10,000×rpm, 10 min, 4° C.), followed by removing the supernatant to wash it. This washing operation was repeated five times. The precipitated red blood cells were re-suspended in 240 μL of PBS (pH=7.4 or 5.5). 20 μL of this red blood cell solution and lipid particles were mixed (the total lipid concentration of the lipid nanoparticles after mixing was 0.2 mM), and the mixture was diluted with PBS of a different pH such that the final volume was 1 mL. The samples were shaken with a ThermoMixer C (Eppendorf) (1,400 rpm, 1 h, 37° C.), and then centrifuged (10,000×rpm, 10 min, 25° C.). 50 μL of the supernatant and 150 μL of ultrapure water were mixed in the wells of a 96-well clear plate, and the absorbance of hemoglobin at an absorption wavelength of 541 nm was measured.

Figure 10:
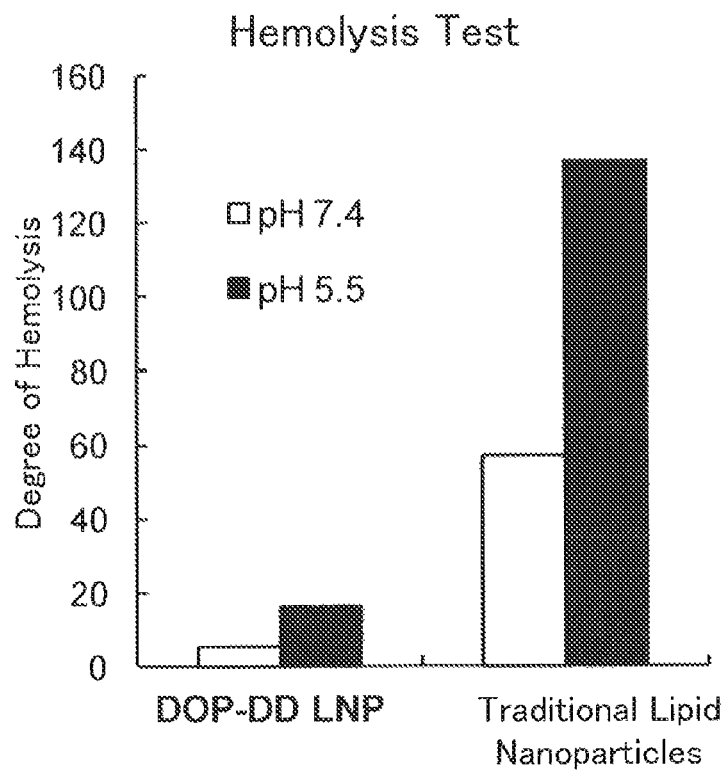
FIG. 10 shows the results of the hemolysis test in Example 8. In the horizontal axis, DOP-DD LNP indicates the results of the lipid particles of Example 8-1, and Traditional Lipid Nanoparticles indicates the results of the control lipid particles of Example 8-2.

FIG. 10 shows the results. The lipid particles prepared using the phospholipid of the present invention, unlike the traditional lipid particles, exhibited no hemolysis under physiological conditions.

Example 9: Production of Lipid Particles and Cytotoxicity Evaluation Test

Example 9-1: Production of Lipid Particles

The procedure of Example 8-1 was repeated using DOP-DD, DPPC, and Chol as lipids, thereby producing lipid particles.

Example 9-2: Production of Lipid Particles

The procedure of Example 8-2 was repeated using DOP-DETA, DPPC, and Chol as lipids, thereby producing control lipid particles.

Example 9-3: Cytotoxicity Evaluation Test

MDA-MB-231 human breast cancer cells were seeded into a 24-well plate (6.0×10$^4$ cells/well), and cultured at 37°

C. for 24 hours. A lipid particle solution (containing 15 pmol of siRNA) was added dropwise to the wells, and the cells were cultured at 37° C. for 24 hours. The cytotoxicity of the lipid particles was evaluated using a Cytotoxicity LDH Assay Kit-WST (Dojindo Laboratories). 50 µL of a lysis buffer was added dropwise to the wells of the positive control group, and the cells were incubated at 37° C. for 30 minutes. 100 µL of the supernatant of each well was transferred to a 96-well clear plate; and 50 µL of a working reagent was added thereto, followed by incubation at room temperature for 30 minutes. Thereafter, 50 µL of a stop solution was added thereto, and the absorbance was measured.

Figure 11:
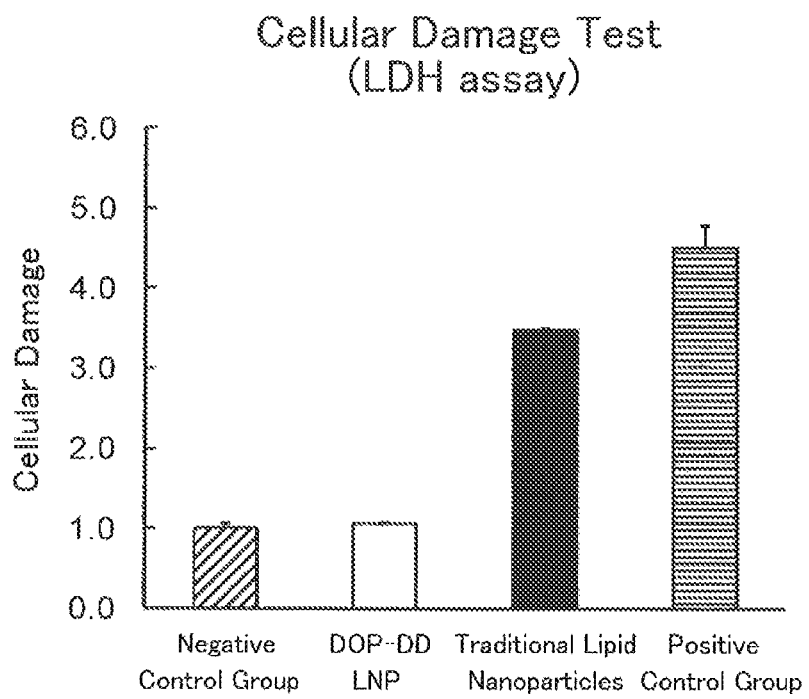
FIG. 11 shows the results of the cytotoxicity evaluation test in Example 9. In the horizontal axis, the Negative Control Group indicates the results of the case in which lipid particles were not used; DOP-DD LNP indicates the results of the lipid particles of Example 9-1; Traditional Lipid Nanoparticles indicates the results of the control lipid particles of Example 9-2; and Positive Control Group indicates the results of the case in which a lysis buffer was added.

FIG. 11 shows the results. The lipid particles prepared using the phospholipid of the present invention, unlike the traditional lipid particles, exhibited no cellular damage under physiological conditions.

Example 10: Production of Lipid Particles and Stability Test

Example 10-1: Production of Lipid Particles

DOP-DD, DPPC, Chol, and polyethylene glycol (M.W. 6,000)-linked distearoyl phosphoethanolamine (DSPE-PEG6000, the amount of which added was 0, 5, or 10 mol % relative to the total lipid amount) were added as lipids to t-butanol, thereby preparing a lipid alcohol solution. Other operations were performed in the same manner as in Example 8-1, thereby producing lipid particles.

Example 10-2: Production of Control Lipid Particles

The procedure of Example 8-2 was repeated using DOP-DETA, DPPC, and Chol as lipids, thereby producing control lipid particles.

Example 10-3: Stability Test on Lipid Particles

100 µL of non-inactivated fetal bovine serum or 100 µL of RNase-free water, 80 µL of lipid particles, and 20 µL of 10× PBS were mixed (the total lipid concentration of the lipid particles after mixing was 1 mM), and shaken with a ThermoMixer C (Eppendorf) (1,000 rpm, 1 h, 37° C.). The absorbance at 600 nm was measured with a SmartSpec™ 3000 (Bio-Rad).

Figure 12:
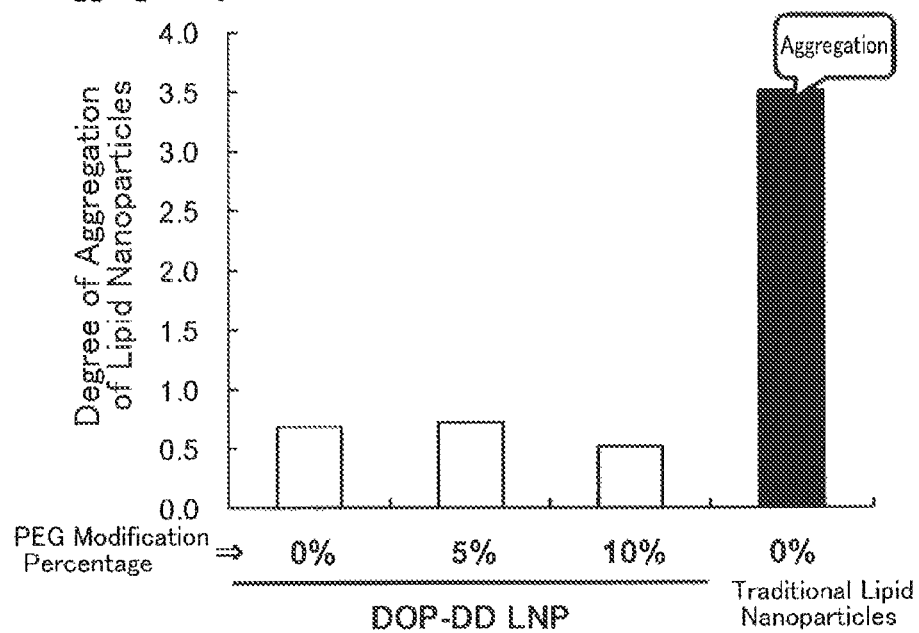
FIG. 12 shows the results of the stability test in Example 10. In the horizontal axis, DOP-DD LNP indicates the results of the lipid particles of Example 10-1, and Traditional Lipid Nanoparticles indicates the results of the control lipid particles of Example 10-2.

FIG. 12 shows the results. The lipid particles prepared using the phospholipid of the present invention, unlike the traditional lipid particles, exhibited high stability, even in the presence of serum. The lipid particles prepared using the phospholipid of the present invention were also confirmed to be stable, regardless of whether PEG modification was present.

Example 11: Production of Lipid Particles and Gene Silencing Test 3

Example 11-1: Production of Lipid Particles

The procedure of Example 8-1 was repeated using DOP-DD, DPPC, and Chol as lipids, thereby producing lipid particles.

Example 11-2: Gene Silencing Test 3

HT1080 human fibrosarcoma cells were seeded into a 6-well plate ($1.5 \times 10^5$ cells/well), and cultured at 37° C. for 24 hours. A lipid particle solution (containing 60 pmol of siRNA) was added dropwise to the wells, and the cells were cultured at 37° C. for 24 hours. The total RNA was extracted from the cells using a TRIzol reagent (Thermo Fisher Scientific), and cDNA was synthesized from the total RNA using a First-Strand cDNA Synthesis Kit (GE Healthcare). The mRNA level of PLK1 was quantified by real-time PCR with cDNA as a template.

Figure 13:
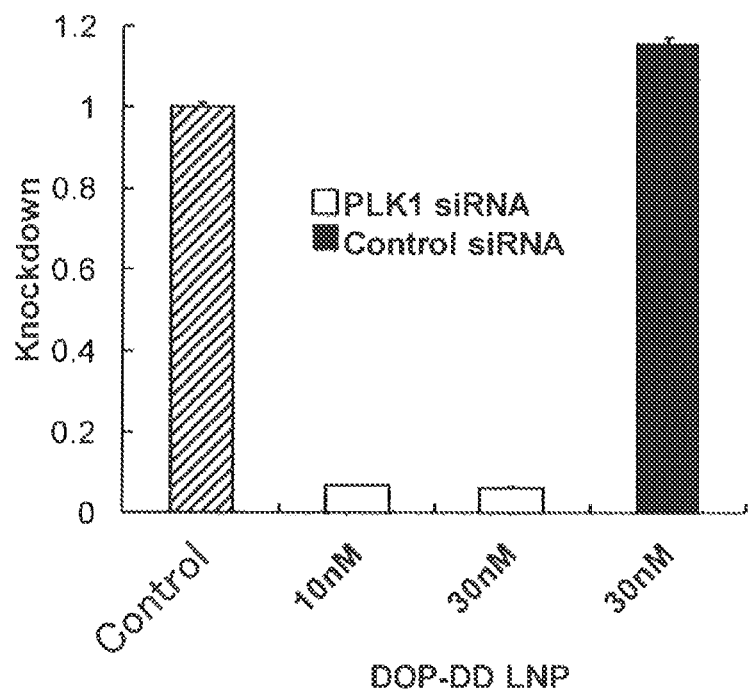
FIG. 13 shows the results of the gene silencing test 3 in Example 11. In the horizontal axis, Control indicates a mock, and DOP-DD LNP indicates the results of the lipid particles of Example 11-1. The white columns indicate the case in which PLK1 siRNA was used as siRNA, and the black column indicates the case in which control siRNA was used as siRNA.

FIG. 13 shows the results. The lipid particles prepared using the phospholipid of the present invention were confirmed to exhibit excellent RNA interference, even at a low concentration of siRNA.

Example 12: Production of Lipid Particles and Gene Silencing Test 4

Example 12-1: Production of Lipid Particles

The procedure of Example 8-1 was repeated using DOP-DD, DPPC, and Chol as lipids, thereby producing lipid particles.

Example 12-2: Gene Silencing Test 4 siRNA was introduced into cells in the same manner as in Example 11-2. The cells having siRNA introduced were dissolved in 0.1% SDS to extract the protein, and the level of PLK1 protein was quantified by western blotting.

Figure 14:
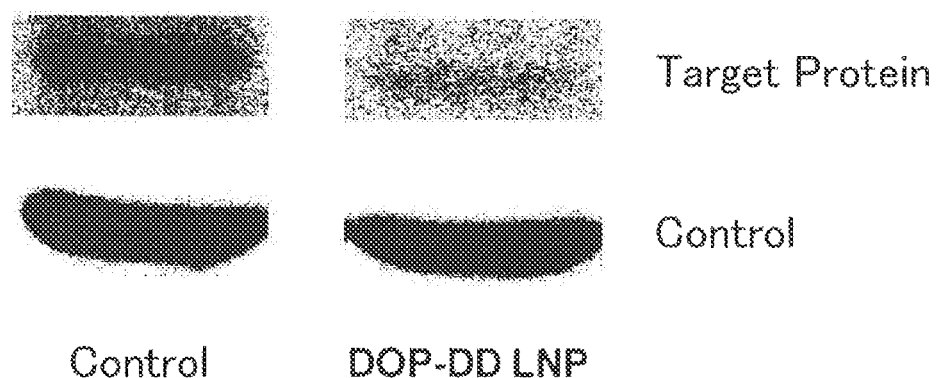
FIG. 14 shows the results of the gene silencing test 4 in Example 12. In the lower part of the photograph, Control indicates the case in which control siRNA was used as siRNA, and DOP-DD LNP indicates the case in which PLK1 siRNA was used as siRNA. On the right side of the photograph, Target Protein indicates the detection results of PLK1, and Control indicates the detection results of the control protein.
Figure 15:
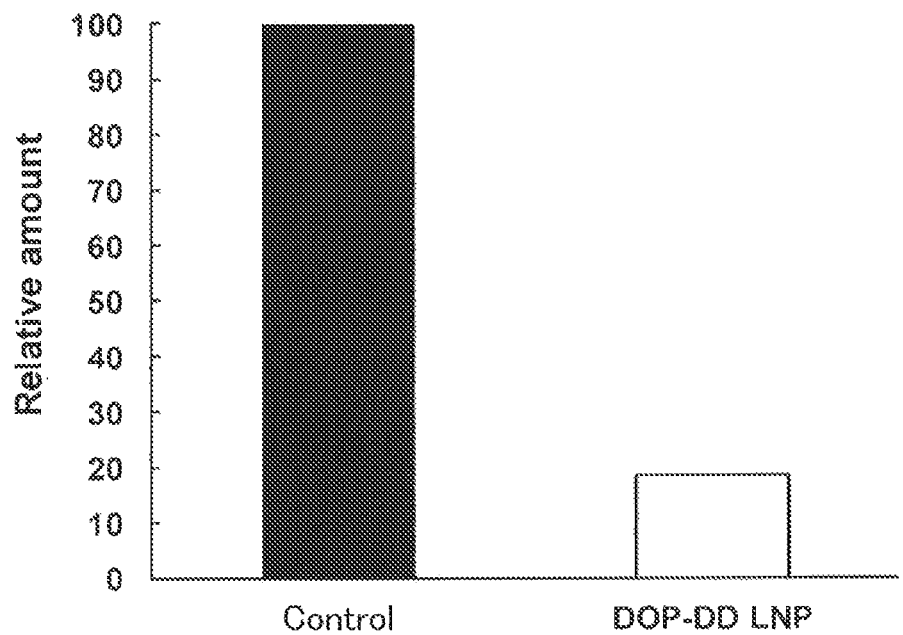
FIG. 15 shows the results of the gene silencing test 4 in Example 12. This figure shows the results of quantified concentration of the bands shown in the upper part of the photograph of FIG. 14.

FIGS. 14 and 15 show the results. The lipid particles prepared using the phospholipid of the present invention were confirmed to exhibit excellent RNA interference, even at a low concentration of siRNA.

Example 13: Production of RI-Labeled Lipid Particles and Biodistribution Test

Example 13-1: Production of RI-Labeled Lipid Particles

DOP-DD, DPPC, Chol, and DSPE-PEG6000 (the amount of which added was 0, 5, or 10 mol % relative to the total lipid amount) as lipids and $^3$H-labeled cholesteryl hexadecyl ether (74 kBq/mouse) were added to t-butanol, thereby preparing a lipid alcohol solution. Other operations were performed in the same manner as in Example 8-1, thereby producing lipid particles.

Example 13-2: Biodistribution Test

Figure 16:
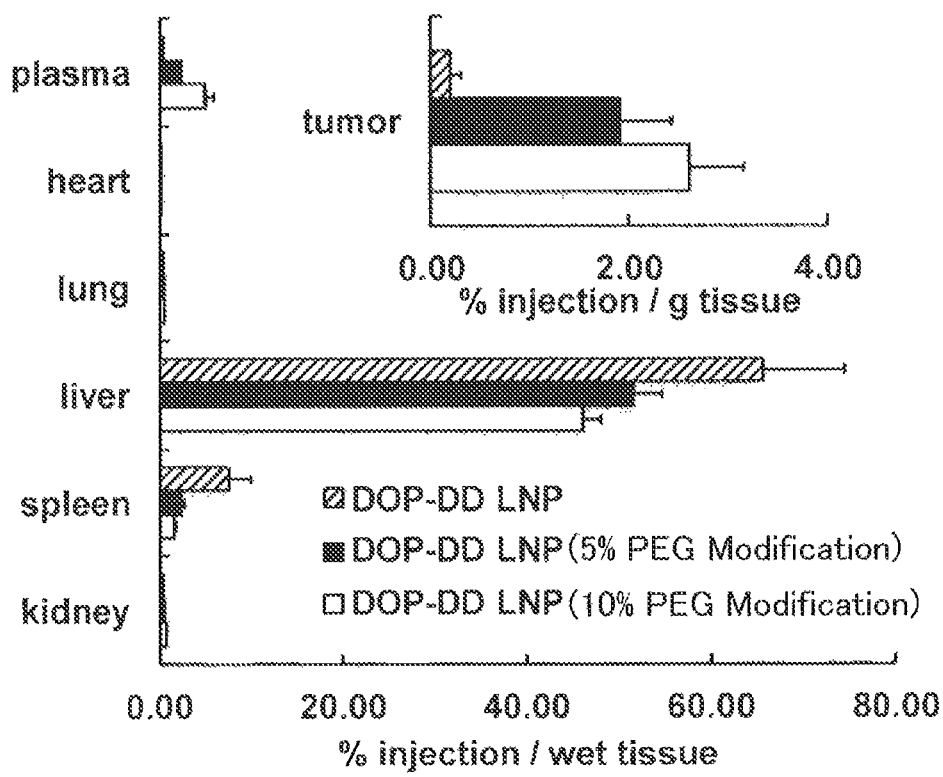
FIG. 16 shows the results of the biodistribution test in Example 13. The vertical axis indicates the organs or tissue about which distribution was examined, and the horizontal axis indicates the proportion of present lipid particles. DOP-DD LNP shows the results of the lipid particles of Example 13-1 by PEG modification percentage (no indication of PEG modification indicates a PEG modification of 0%).

An MDA-MB231-cell suspension ($1.0 \times 10^7$ cells/100 µL PBS) was subcutaneously transplanted into BALB/c nu/nu mice, and the mice were reared until a tumor volume grew to 200 mm$^3$. A lipid particle solution (containing 2 µg of siRNA and 74 kBq of [$^3$H]-cholesteryl hexadecyl ether) was administered to the mice through their caudal vein, and the mice were reared for 24 hours. Thereafter, organs such as blood, heart, lung, liver, spleen, kidney, and tumor were isolated, and these organs were dissolved in 1 mL of Solvable. 500 µL of 2-propanol (an antifoaming agent) and 500 µL of hydrogen peroxide (a decolorant) were added thereto, and then the organs were allowed to stand overnight. 10 mL of a scintillator (Hionic-Fluor, PerkinElmer) was further added, and a reaction was allowed to proceed well. The reaction products were allowed to stand overnight in a dark place to stabilize the phosphorescence. The $^3$H radioactivity was measured with a liquid scintillation counter (LSC-7400, Hitachi Aloka Medical). FIG. 16 shows the results. The lipid particles prepared using the phospholipid of the present invention were confirmed to exhibit increased accumulation in tumors due to PEG modification.

Example 14: Production of Lipid Particles and Gene Silencing Test In Vivo

Example 14-1: Production of Lipid Particles

DOP-DD, DPPC, Chol, and DSPE-PEG6000 (the amount of which added was 10 mol % relative to the total lipid amount) as lipids were added to t-butanol, thereby preparing a lipid alcohol solution. Other operations were performed in the same manner as in Example 8-1, thereby producing lipid particles.

Example 14-2: Gene Silencing Test In Vivo

A suspension of MDA-MB-231 human breast cancer cells ($1.0 \times 10^7$ cells/100 µL PBS) was subcutaneously transplanted into BALB/c nu/nu mice, and the mice were reared until a tumor volume grew to 150 mm$^3$. A lipid particle solution (containing 20 µg of siRNA) was administered to the mice through their caudal vein, and the mice were reared for 96 hours. Their tumors were isolated, and the total RNA was extracted using a TRIzol reagent (Thermo Fisher Scientific). cDNA was synthesized from the total RNA, and the mRNA level of PLK1 was quantified by real-time PCR with cDNA as a template.

Figure 17:
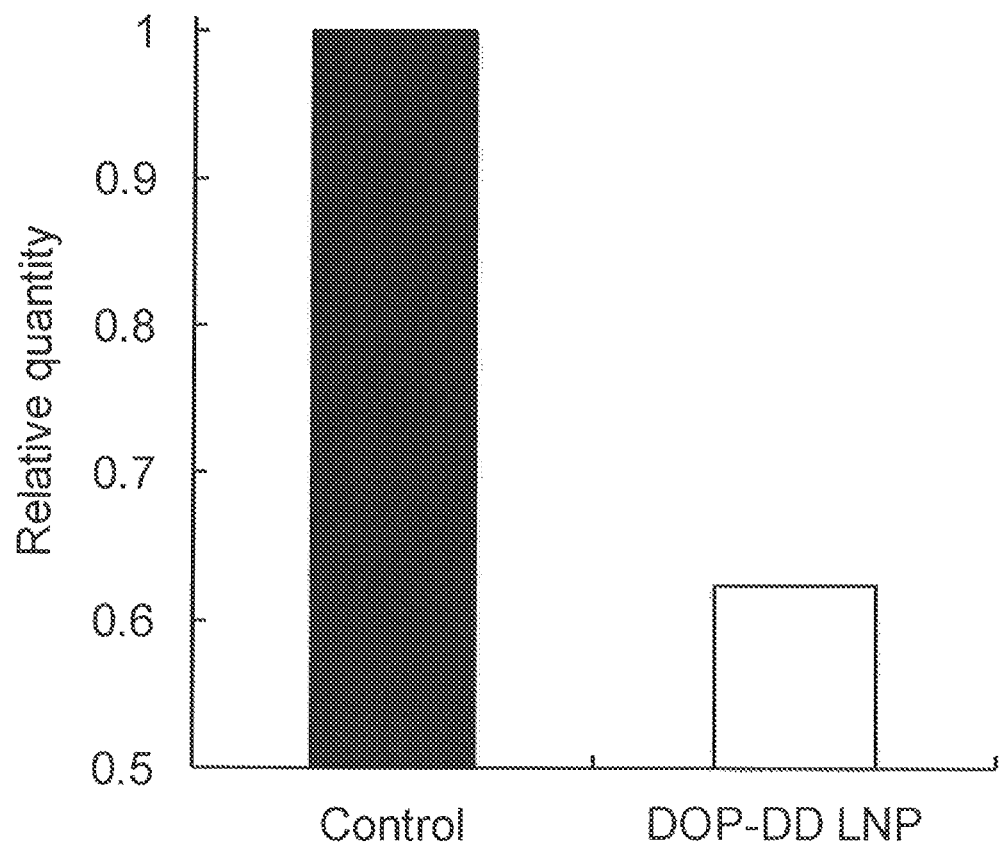
FIG. 17 shows the results of the gene silencing test in vivo in Example 14. In the horizontal axis, Control indicates the case in which control siRNA was used as siRNA, and DOP-DD LNP indicates the case in which PLK1 siRNA was used as siRNA.

FIG. 17 shows the results. The lipid particles prepared using the phospholipid of the present invention were confirmed to induce RNA interference in tumors.

The invention claimed is:

1. A phospholipid represented by formula (1):

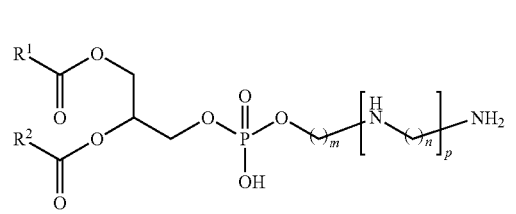

(1)

wherein $R^1$ and $R^2$ are identical or different, and represent a chain hydrocarbon group, m represents 1 or 2, n represents 1 or 2, and p represents an integer of 1 to 4.

2. The phospholipid according to claim 1, wherein the chain hydrocarbon group is an unsaturated chain hydrocarbon group.

3. The phospholipid according to claim 1, wherein the chain hydrocarbon group has 12 to 24 carbon atoms.

4. The phospholipid according to claim 1, wherein m and n are both 2.

5. The phospholipid according to claim 1, wherein p is 1 or 2.

6. A lipid particle comprising the phospholipid of claim 1, the phospholipid being a first phospholipid.

7. The lipid particle according to claim 6, in which a polynucleotide is encapsulated.

8. The lipid particle according to claim 6, further comprising cholesterol.

9. The lipid particle according to claim 6, further comprising a second phospholipid, the second phospholipid being a phosphatidylcholine, wherein the first phospholipid has an unsaturated chain hydrocarbon group.

10. The lipid particle according to claim 9, wherein the second phospholipid is present in an amount of 30 to 70 mol, per 100 mol of the first phospholipid.

11. A method for producing a lipid particle, the method comprising mixing an alcohol solution containing the phospholipid of claim 1 with an acid aqueous solution containing a water-soluble polynucleotide.

12. The method according to claim 11, wherein the alcohol solution contains butanol as a solvent.

13. A medical drug comprising a lipid particle containing the phospholipid of claim 1, and a polynucleotide.

* * * * *